United States Patent [19]

Capuano et al.

[11] 4,151,255

[45] Apr. 24, 1979

[54] pH MONITOR WITH AUTOMATIC BUFFER STANDARDIZATION

[76] Inventors: Italo A. Capuano, Orange; Edward G. Miller, East Haven, both of Conn.

[21] Appl. No.: 841,187

[22] Filed: Oct. 11, 1977

[51] Int. Cl.$^2$ .................. G01N 31/16; G01N 27/30
[52] U.S. Cl. .................................. 422/76; 204/1 T;
204/195 F; 324/30 R; 422/62
[58] Field of Search ............ 23/253 R, 230 R, 253 A,
23/230 A; 204/195 T, 195 F, 1 T; 324/30 R;
422/75, 76, 62

[56] References Cited
U.S. PATENT DOCUMENTS

| | | |
|---|---|---|
| 3,489,520 | 1/1970 | Chartouni et al. ................ 23/253 R |
| 3,556,950 | 1/1971 | Dahms ................................ 23/253 R |
| 3,625,655 | 12/1971 | Culp et al. ......................... 23/253 R |
| 4,018,565 | 4/1977 | Fletcher et al. ............... 23/230 R X |

OTHER PUBLICATIONS

Technical Bulletin #4, Great Lakes Instruments, Inc., 1973.

*Primary Examiner*—R. E. Serwin

[57] ABSTRACT

An apparatus for monitoring the pH of a sample source is disclosed. The apparatus has a sample chamber to which fluid is fed from the sample source for pH monitoring. An automatic rinse and buffer standardization system automatically, periodically standardizes the apparatus against a buffer solution of known pH.

19 Claims, 4 Drawing Figures

PH MONITOR WITH AUTOMATIC BUFFER STANDARDIZATION

The predominant type of pH monitor in commercial use presently for monitoring the pH of a sample source, such as chemical reaction inlet or outlet streams, is one in which two electrodes, a glass electrode and a reference electrode are placed within the sample source and are connected to a pH meter and associated recorder to provide a continuous record of the pH of the sample source. However, the fluid within the sample source can be, and often is, of a type which may attack the glass and reference electrodes and thus alter the electrodes sufficiently to result in incorrect pH readings and thereby defeat the function of the pH meter. This can in part be corrected by a regular process of removing the electrodes and replacing them if damaged. However, such replacement and removal may require shutting down the chemical reactor and thus prevent continuous reactor operation.

Also, where very precise pH measurements are desired, there is a need for a more precise method of checking accuracy intermittently so as to be better assure that accurate readings are being given by the pH monitor. Further, there is a need for a device which can automatically do such checking and for a device which will automatically correct for any inaccuracies. A part of the invention resides in the recognition of these needs.

A solution to these problems is the apparatus of the invention which provides an apparatus for monitoring the pH of a sample source, comprising:

a. sample feed means, for selectively withdrawing a fluid sample from said sample source and supplying said withdrawn fluid sample to said apparatus, b. test chamber means, in fluid communication with said sample feed means, for receiving said fluid sample and containing said fluid sample during said monitoring, c. pH measuring means for selectively measuring the pH of said contained fluid sample, d. sample removal means, for removing said fluid sample from said test chamber means, and e. automatic buffer standardization means for automatically periodically standardizing said pH measuring means against a buffer solution of known pH.

The apparatus of this invention is more fully described, by way of example, in the attached drawings in which.

Referring now to the above figures in more detail, by way of example, a preferred embodiment of the invention will be described.

Figure 1:
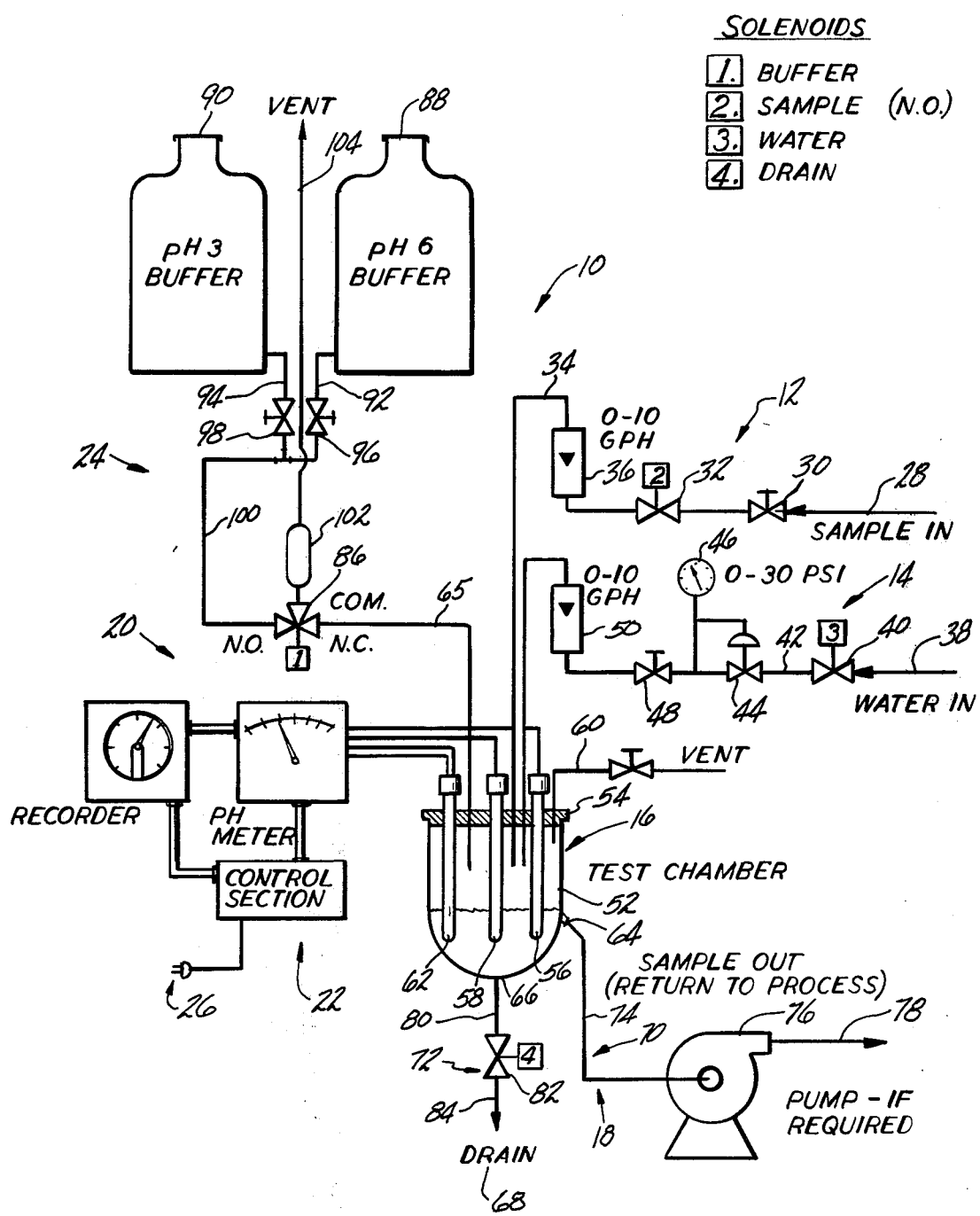
FIG. 1 is a flow diagram showing a preferred pH analyzer embodying the invention.

FIG. 1 is a flow diagram of a pH analyzer 10. Analyzer 10 comprises sample feed means 12, rinse feed means 14, test chamber means 16, sample exhaust means 18, pH measuring means 20, control means 22, buffer supply means 24 and power connector means 26 (410 of FIG. 4).

Sample feed means 12 includes an inlet line 28, a throttle valve 30, a solenoid shut-off valve 32, an outlet line 34 and a flow meter 36. While the sample means 12 is shown in FIG. 1 with inlet line 28 leading from a sample source (not shown) to solenoid valve 32 via throttle valve 30 and with outlet line 34 leading from solenoid valve 32 to test chamber 16 via flow meter 36, the particular order in which valves 30 and 32 and flow meter 36 are placed in sample feed means 12 can be varied as desired. Also, the throttle valve 30 or flow meter 36 could be eliminated for applications where adjustable sample flow rate is not desired or where there is no desire to know the flow rate. In most applications, throttle valve 30 and flow meter 36 will be desired in order to keep accurate control and record of the amount of sample fluid removed from the sample source. This is especially true where the sample source is a chemical reaction chamber or a supply or product line of a chemical reactor where the quantity of sample fluid withdrawn or added could be of importance to the overall efficiency of the chemical reactor. Throttle valve 30 and solenoid valve 32 are preferably lined with a chemically inactive protective lining, such as for example polytetrafluoroethylene, in order to provide ability to handle caustic or acidic or otherwise chemically active sample fluids. Flow meter 36 is an all-glass flow meter marked in suitable units, such as for example 0–10 gallons per hours (GPH), although flow meter 36 could be plastic or metallic or even unmarked, if so desired. Lines 28 and 34 are clear, flexible, plastic-like tubing of a chemically inactive material but could be metallic or glass or even inflexible, if so desired. Solenoid valve 32 serves to selectively allow or prevent flow from line 28 to line 34 while throttle valve 30 controls the flow rate through lines 28 and 34 when valve 30 is open, the flow rate through line 34 being visually indicated on flow meter 36.

Rinse feed means 14 comprises rinse inlet line 38, solenoid valve 40, rinse outlet line 42, constant pressure valve 44, pressure gauge 46, throttle valve 48 and flow meter 50. Although rinse inlet line 38 is shown as leading to solenoid valve 40 from a source of rinse fluid (not shown) and rinse outlet line 42 is shown leading to test chamber 16 through constant pressure valve 44, throttle valve 48 and flow meter 50, the precise order of valves 40, 44 and 48 and flow meter 50 can be varied as desired. As with valves 30 and 32 of sample feed means 12, valves 40, 44 and 48 are preferably provided with a chemically inactive lining such as polytetrafluoroethylene or other suitable material. As an alternative, valves 40, 44 and 48 could be provided without linings, if so desired. Lines 38 and 42 are chemically inactive, flexible, plastic-like tubing or could be metallic or glass tubing, if desired. Throttle valve 40 is normally closed and serves to selectively prevent and allow rinse fluid to pass from line 38 to line 42 in response to the absence or presence, respectively, of an actuating signal. Constant pressure valve 44 serves to regulate the flow through line 42 so as to achieve a constant desired pressure in line 42. Throttle valve 48 serves to regulate the flow rate in line 42 when valve 40 is open and flow meter 50 serves to indicate the flow rate in line 42. In most applications, throttle valve 48 and constant pressure valve 44 will be included in rinse feed means 14, however, constant pressure valve 44, throttle valve 48 and flow meter 50 can be deleted when the rinse fluid source (not shown) leading to line 38 incorporates suitable constant pressure regulation or flow rate indication. Unlike valves 30 and 32, it is not normally necessary that valves 40, 44 and 48 be lined with a chemically inactive material, since the normal rinse fluid is water. However, for long life it is preferable to nevertheless line valves 40, 44 and 48 as indicated.

Test chamber 16 includes vessel 52, top 54, electrodes 56, 58 and 62 and vent means 60. Test chamber means 16 is connected to sample exhaust means 18, sample feed means 12, rinse feed means 14, pH measuring means 20 and buffer supply means 24. Vessel 52 is a cylindrical glass vessel. Top 54 is a disc-like polytetrafluoroethylene body containing appropriate sized holes or openings to support electrodes 56 and 58 and a temperature compensation electrode 62, as well as lines 34 and 42 of sample feed means 12 and rinse feed means 14, respectively. Top 54 also contains suitable openings for gas vent 60 and an outlet line 65 of buffer supply means 24. Vessel 52 has an overflow opening 64 at a predetermined point on the side thereof and a drain outlet 66 at the bottom thereof. Vessel 52 serves to hold a predetermined quantity of sample fluid or buffer fluid, the level of such fluid being determined by the height of overflow opening 64 above the bottom of vessel 52. Sample fluid selectively enters vessel 52 through line 34 and overflows through overflow opening 64 from which it is returned to the sample source (not shown) by sample exhaust means 18, if desired. Alternatively, the sample fluid may be exhausted to a drain 68 through drain outlet 66 and sample exhaust means 18. Vessel 52 is preferably glass in order to allow visual observation of the operation of electrodes 56, 58 and 62 during pH measurement and standardization operations described below. Electrode 56 is a glass electrode for measurement of pH of the sample fluid contained within vessel 52 and electrode 58 is a reference electrode for use in such measurement. Temperature compensation electrode 62 serves to provide a compensation signal to a pH measuring means 20 in order to compensate for variations in the temperature of the sample fluid within vessel 52.

Sample exhaust means 18 includes sample return means 70 and sample drain means 72. Sample return means 70 comprises a return inlet line 72, pump means 76 and return outlet line 78. Sample fluid entering overflow opening 64 passes into return inlet line 74, which is connected thereto, and enters pump means 76 from which the sample to be returned is pumped through return outlet line 78 back to the sample source (not shown) if desired. Sample drain means 72 includes drain inlet line 80, drain solenoid valve 82 and drain outlet line 84. Sample fluid enters drain inlet line 80 and selectively passes through drain solenoid valve 82 and into drain outlet line 84 which leads to drain 68. Lines 80 and 84 are preferably flexible, chemically inactive, plastic-like tubing and drain solenoid valve 82 is preferably lined with a chemically inactive material, such as for example, polytetrafluoroethylene. Similarly, return inlet line 74 and return outlet line 78 are preferably a chemically inactive tubing and pump means 76 is preferably lined with a chemically inactive material. These protective linings serve to prolong the useful life of sample exhaust means 18 and to prevent contamination of the sample source (not shown) during the continuous or intermittent pH analysis operations performed by the invention. The pH measuring means 20 is a conventional pH meter and recorder combination, such as for example, a Leeds and Northrup industrial Model 7070-01 temperature compensating pH meter and a Leeds and Northrup Model H circular chart recorder or similar pH meter and recorder. The particular circuitry of pH measuring means 20 will not be described except with respect to the connection of the various terminals of pH measuring means 20 with control unit 22, solenoid valves 30, 44, 82 and 86 (described below) and electrodes 56, 58 and 62.

Control unit 22 is an automatic timing unit which automatically controls the sequential operations of the various components of pH analyzer 10 in order to provide automatic periodic buffer standardization and continuous pH monitoring operations, as described below.

Buffer supply means 24 comprises buffer storage means 88 and 90, buffer supply lines 92 and 94, buffer throttle valves 96 and 98, buffer common line 100, buffer solenoid valve 86, buffer storage bulb 102, buffer outlet line 65 and buffer vent 104. Buffer storage means 88 and 90 are bottles, each containing a standard buffer solution for use in standarizing the reading of pH measuring means 20 during the intermittent automatic buffer standardization of the invention. Two separate buffer storage means are provided since the preferred pH measuring means has two different measurement scales having two different central points. The pH of the solution stored in storage means 88 is selected so as to serve as a reference for the midpoint or central point of the first scale, and the pH of the buffer solution stored in storage means 90 is selected so as to provide a reference for the midpoint or central point of the second scale of pH measuring means 20. Storage means 88 and 90 are connected through buffer supply lines 92 and 94 and buffer throttle valves 96 and 98, respectively, to buffer common line 100. Buffer common line 100 is in turn connected to buffer outlet line 65 and buffer storage bulb 102 through buffer solenoid valve 86. Buffer solenoid valve 86 is a three-way solenoid operated valve normally open to flow from buffer common line 100 to buffer storage bulb 102 and normally closed to flow from common line 100 to line 65. When actuated, solenoid valve 86 allows flow from line 100 to line 65 and prevents flow from line 100 to bulb 102. As with solenoid valves 32, 40 and 82, solenoid valve 86 is controlled by control unit 22. Lines 92, 94, 100 and 65 are preferably flexible, chemically inactive, plastic-like tubing and valves 96, 98 and 86 are preferably polytetrafluoroethylene-lined in order to provide longer useful life. However, metallic or glass flexible or nonflexible tubing could be substituted, if desired, if the buffer solution stored in buffer storage means 88 and 90 is normally be relatively inactive. In the event the midpoint of either of the scales of pH measuring means 20 is relatively high (basic or caustic) or relatively low (acidic) it would be most preferable to have chemically inert flow lines and valves in buffer supply means 20. Valves 96 and 98 serve to selectively open and close flow from lines 92 and 94 to line 100 in order to provide a supply of the buffer solution of storage means 88 or 90, respectively, to common line 100. This supplied buffer solution will flow through common line 100 and normally open solenoid valve 86 into bulb 102 and vent line 104 until equilibrium is achieved or the open one of throttle 96 and 98 is closed to prevent further supply of buffer solution to bulb 102. Normally, valve 96 or 98 will be only slightly open an amount just sufficient to supply enough buffer solution to completely fill bulb 102 during the interval of time valve 86 is not actuated so that a complete bulb of buffer solution will be provided to outlet line 65 upon the automatic actuation of valve 86 by control unit 22, or valves 96 or 98 can be fully opened.

Figure 2:
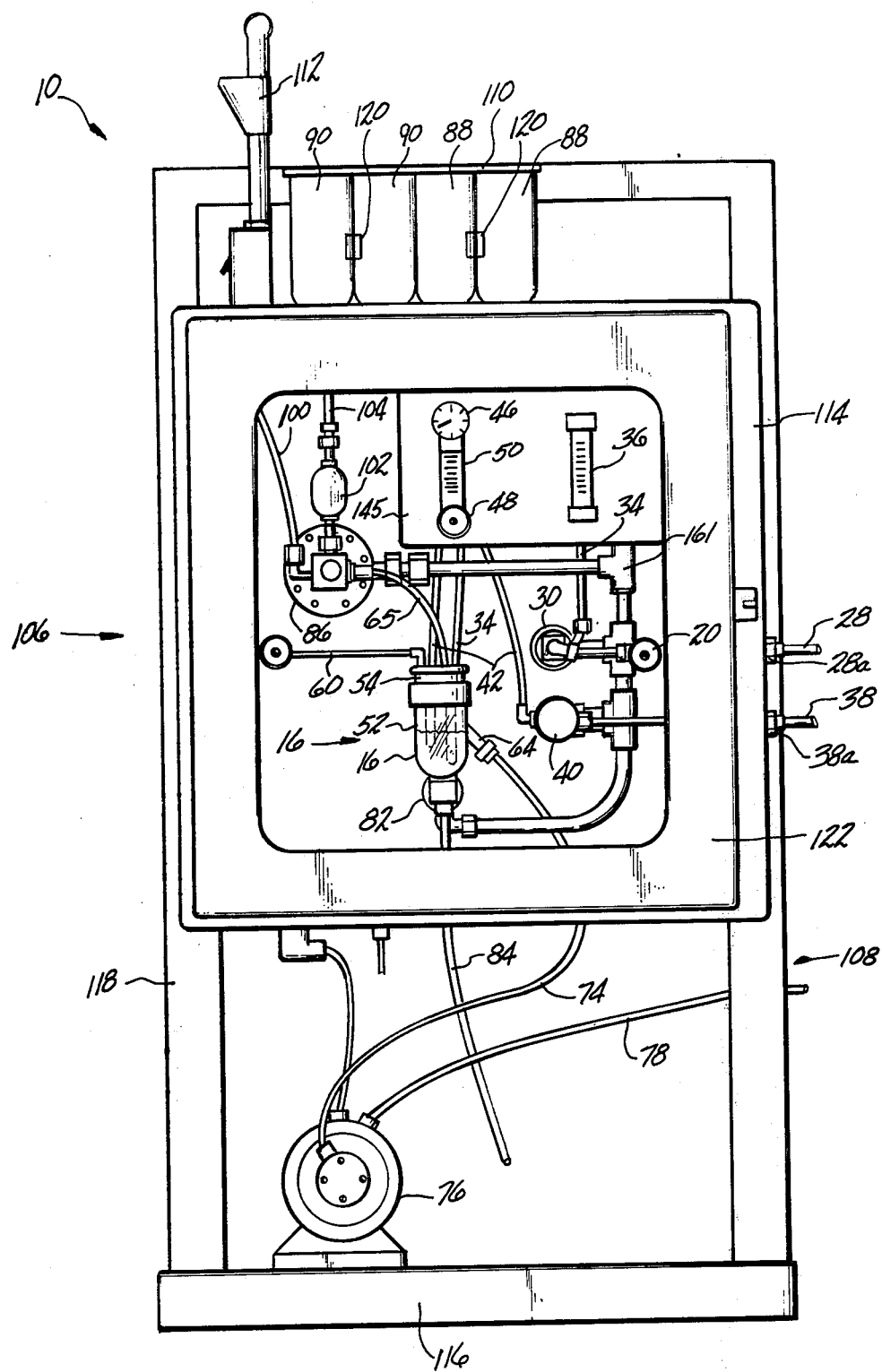
FIG. 2 is a back elevational view of the pH analyzer of FIG. 1 showing a typical housing structure.

FIG. 2 is a back elevational view of pH analyzer 10 of FIG. 1 showing a typical housing structure 106 which includes a framework 108, a buffer storage rack 110, a power inlet 112 and a body 114. Framework 108 is an L-shaped support comprised of a horizontal hollow rectangular base with a hollow vertical frame portion 118 projecting upwardly therefrom. Base 116 and portion 118 are integral welded bars. Other frameworks could be equally suitable for supporting the invention. A body 114 is attached by welds or bolts (not shown) to portion 118 and storage rack 110 is attached to an upper surface of body 114. Suitable openings are provided in body 114 for the various inlets and outlets such as lines 28, 38, 74, 84, 92, 94, and 60. Power inlet 112 leads into control unit 22 (see FIG. 1). Rack 110 has suitble spring clips 120 to hold buffer storage means 88 and 90. Body 114 can be provided with a door 122 to facilitate access to analyzer 10 for maintenance.

Also shown in FIG. 2 is a preferred embodiment of many of the components of analyzer 10 of FIG. 1. Unlike FIG. 1, however, these components are shown substantially as they could appear rather than schematically. Sample inlet line 28 and rinse inlet line 38 are seen entering body 114 through suitable bulkhead fittings 28a and 38a and connect to valves 20 and 40, respectively. Also shown is test chamber 16 and the vessel 52, top 54, overflow opening 64, and vent 60 thereof with associated lines 65, 34, 42, 74, and 84 and valves 30, 48, 82, and 86. Also, common line 100, bulb 102 and vent line 104 are seen.

Figure 4:
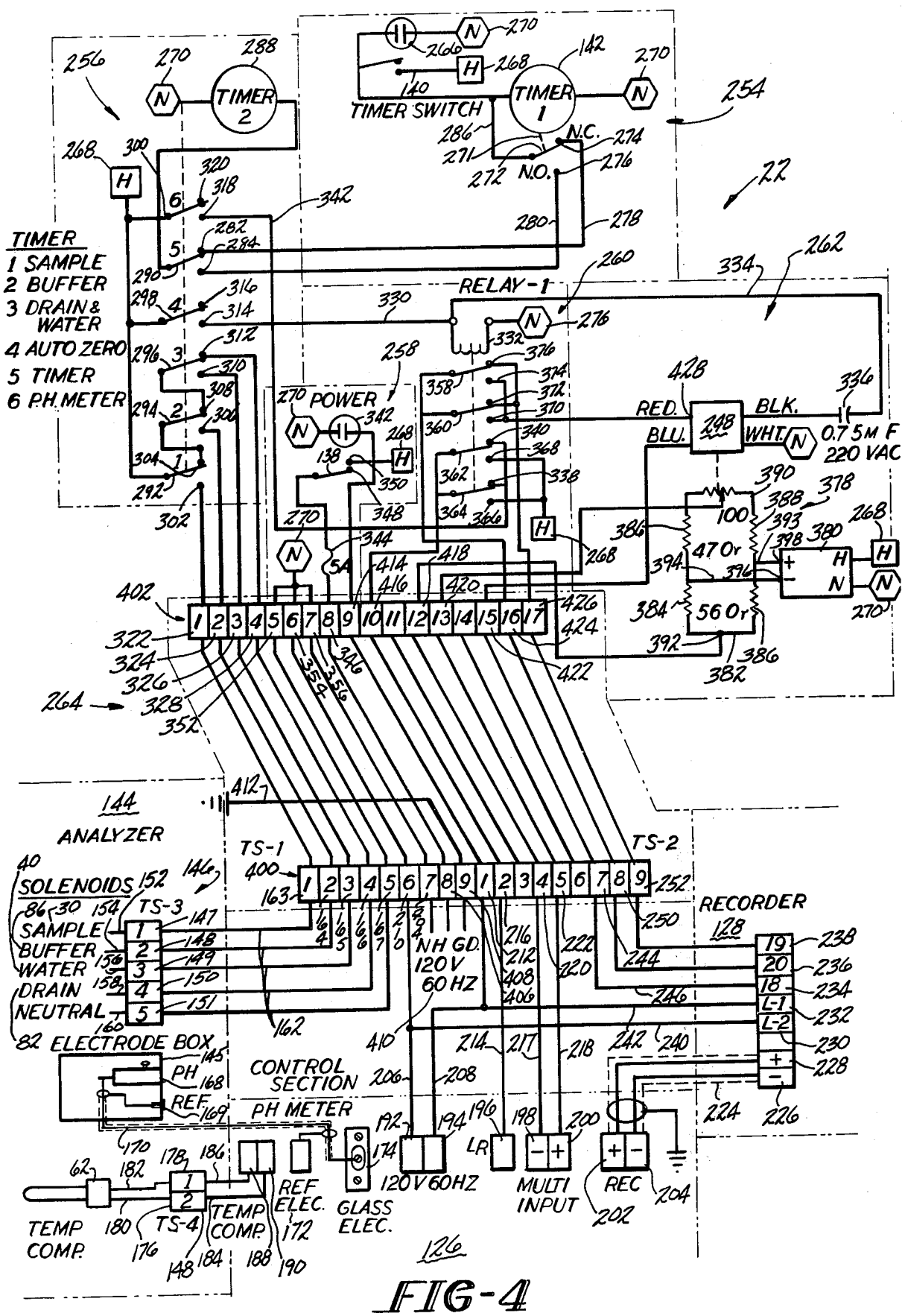
FIG. 4 is a schematic circuit diagram of a preferred electrical system usable to control the analyzer of FIG. 1.

Referring now to FIGS. 2 and 4, flow meters 36 and 50 are seen mounted on the back of an electrode box 145.

A conduit 161 is seen leading from electrode box 145, which also encloses terminal 147-151 to solenoid valves 30, 40, 82 and 86. Conduit 161 encloses wires 152, 154, 156, 158, and 160.

Figure 3:
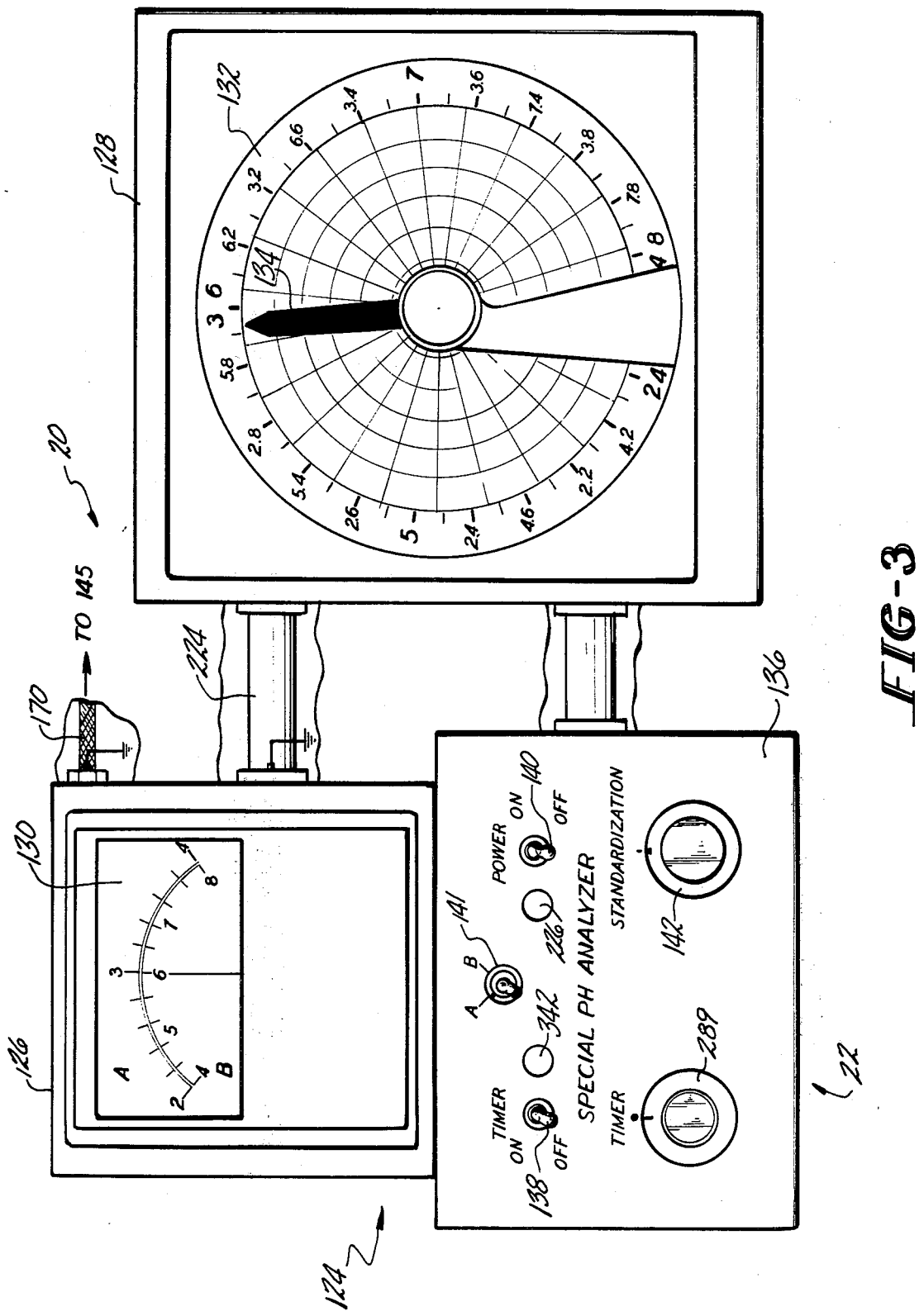
FIG. 3 is a front view of a portion of the analyzer of FIG. 2 showing a typical pH meter and recorder.

FIG. 3 is a front view of a control panel portion 124 of analyzer 10 of FIG. 1. Control portion 124 includes pH measuring means 20 and control unit 22. The pH measuring means 20 further includes a pH meter 126 and a recorder 128. Meter 126 comprises a typical needle-type display 130 and various internal components (not shown). Recorder 128 includes a recording disc 132 and pointer/scribe 134 and various internal components not shown. Control unit 22 includes a front panel 136 and internal components (see FIG. 4) described below. Control panel 136 includes a power on-off switch 138, a timer manual switch 140, a timer auto switch 142, a scale selector 141, power and timer indicator lights 226 and 342 and a timer setting knob 289. Scale 130 is a double scale having individual scale portions A and B which are each set at a different selected range such as for example 2-4 for portion A and 4-8 for portion B. Switch 141 is operable to select either scale A or B.

FIG. 4 is a schematic diagram showing a preferred electrical circuit for use with analyzer 10 of FIGS. 1-3 and in particular shows electrical circuitry for control unit 22 and shows the inter-connecting wiring between circuit means 22, pH meter 126, recorder 128 and analyzer section 144. Analyzer section 144 comprises solenoid valves 30, 40, 82, and 86, electrode box 145, and two terminal sets 146 and 148. Terminal set 146 has at least four separate terminals 147, 148, 149 and 150 and can also have any number of additional neutral terminals 151 to allow a two-wire connection to each of solenoid valves 30, 40, 82 and 86. A first wire 152, 154, 156 or 158 connects terminals 147, 148, 149 and 150 with solenoid valves 30, 86, 40 and 82, respectively. A second wire 160 connects each of valves 30, 40, 82 and 86 with neutral terminal 151 to complete the two-wire connection. Control unit 22 selectively opens or closes an electrical connection which provides current to selective ones of terminals 147-150. Neutral terminal 151 could be deleted if a direct current one-wire cnnection were used and solenoid valves 30, 40, 82 and 86 were grounded. However, the presence of terminal 151 allows AC current operation, such as for example by the common 120 volt, 60 hertz current commercially available in the USA. A 5-wire conduit 162 connects terminals 147-151 to below described terminals 163-167 of control unit 22 to allow such selective circuit opening and closing by control unit 22.

Electrode box 145 includes a connection 168 leading to glass electrode 56 and a second connection 169 leading to reference electrode 58. A cable 170 is connected to connections 168 and 169 and leads to terminals 172 and 174 of pH meter 126. Cable 170 is separate from conduit 162 and is insulated and preferably grounded to isolate the electrode signals emanating from electrodes 56 and 58. Analyzer section 144 also includes terminal set 148 which has two separate terminals 176 and 178 connected by lead wires 180 and 182 to temperature compensation electrode 62. Terminals 176 and 178 are also connected by wires 184 and 186 to temperature compensation input terminals 188 and 190 of pH meter 126. Temperature compensation electrode 62, in cooperation with lead wires 180-186, serves to generate a signal to terminals 188 and 190, said signals being indicative of the temperature within test chamber means 16. The pH meter 126, as indicated above, can be any suitable pH meter, such as for example, a Leeds and Northrup industrial pH meter Model 7070-01. pH meter 126 includes a terminal section having a plurality of teminals 188, 190, 172, 174, 192, 194, 196, 198, 200, 202 and 204. Terminals 188 and 190 are connected to temperature compensation circuitry (not described) within pH meter 126 which circuitry serves to compensate for variations in the temperature within test chamber 16 so as to produce a pH measurement independent of the test chamber temperature. Terminals 172 and 174 are the input terminals providing the pH indicative signal to pH meter 126 under normal operations. Terminal 174 receives a primary signal while reference electrode terminal 172 receives a reference signal. pH meter 126 operates to transmit this primary signal and reference signal into an output proportional to the pH within test chamber 16. Terminals 192 and 194 provide power current to pH meter 126 in order to allow operation thereof. Terminals 192 and 194 are connected by power leads 206 and 208 to terminals 210 and 212 of control unit 22, as below described. Terminal 196 is a terminal leading to a standby relay (not shown) within pH meter 126. This standby relay serves to place pH meter 126 in a standby condition when power is supplied to terminal 196. This standby condition results in the input from terminals 172 and 174 being disconnected from pH meter 126 so the pH meter is forced to produce a normal or mid-scale output when terminal 196 receives power. Terminals 198 and 200 are connected to range adjustment means (not shown) within pH meter 126 and serve to apply a "bucking voltage" to the input of pH meter 126 in order to result in an output of a given pH range. Terminals 202 and 204 are output terminals which provide an output signal proportional to the signals received by terminals 172 and 174 so long as the pH meter is not in standby position, i.e. so long as power is not received by terminal 196. Terminal 196 is connected by wire 214 to terminal 216 of control unit 22, for reasons described below. Terminals 198 and 200 are connected by wires 217 and 218 to terminals 220 and 222 of control unit 22 for receiving a suitable signal from control unit 22 to set the range of the output of pH meter 126. Output terminals 202 and 204 are connected by a grounded cable or conduit 224 to input terminals 226 and 228 of recorder 128 to provide a signal to recorder 128 indicative of the pH within test chamber 16 during normal operation.

Recorder 128 can be any suitable recording device such as a Leeds and Northrup Model H circular chart recorder, as above noted. Recorder 128 serves to provide a continuous record of the pH within test chamber 16. Recorder 128 includes a terminal section having terminals 226, 228, 230, 232, 234, 236, and 238. Terminals 226 and 228 provide the input to a suitable amplifier within recorder 128 while terminal 236 serves to receive the output of the recorder amplifier within recorder 128. Terminals 230 and 232 are connected to wires 206 and 208, respectively, by wires 240 and 242 in order to provide power current to recorder 128. Terminal 234 is connected to a ground terminal (not shown) of the amplifier (not shown) of recorder 128. Terminal 234 is also connected to terminal 244 of control unit 22 by wire 246 in order to ground the auto zero motor 248 (described below) of control unit 22. Terminal 236 is also connected to terminal 250 of control unit 22 and terminal 238 is connected to terminal 252 of control unit 22. Terminal 238 is the input of a servomotor within recorder 128. The servomotor (not described) serves to move a scribe 134 of recorder 128 to produce a line indication indicative of the pH signal received by terminals 226 and 228.

Control unit 22 includes first timer section 254, a second timer section 256, a power section 258, a relay section 260, an auto zero section 262 and a terminal section 264. First timer section 254 includes a timer manual switch 140, a timer auto switch 142 and a timer indicator light 266. Timer manual switch 140 is connected to first power terminal 268 of power section 258 and to timer indicator light 266 and timer auto switch 142. Timer indicator light 266 and timer auto switch 142 are in turn connected to second power terminal 270 of power section 258 to complete an electrical circuit when timer manual switch 140 is closed. Timer manual switch 140 is a normally open contact-making electrical switch and serves to initiate the operation of timer auto switch 142. Timer indicator light 266 serves to indicate when timer switch 140 is closed and hence when timer auto switch 142 is in operation. Timer auto switch 142 includes a relay 271 which operates after a predetermined time to move a two position switch 272 from a first position contacting a first terminal 274 to a second position contacting a second terminal 276. Terminals 274 and 276 are connected by wires 278 and 280 to terminals 282 and 284 of second timer section 256, respectively, for reasons described below. Switch 272 is connected to timer manual switch 140 by wire 286 and serves to transmit current between switch 140 and wire 278 when switch 140 is in the normal position.

Second timer section 256 is a multiple, time delay, cam-operated relay which serves to open and close electrical circuits leading to terminals 147-150 in order to control the opening and closing of solenoid valves 30, 86, 40 and 82. Second timer section 256 includes a timer 288 which is connected to terminal 270 and separately to a switch 290, described below. Switch 290 is normally connected to terminal 282, which is in turn connected by wire 278, terminal 274, switch 272, wire 286 and switch 140 to terminal 268 thus completing an electrical circuit through timer 288. When timer auto switch 142 actuates relay 270 to move switch 272 from contact with terminal 274 into contact with terminal 276, the electrical circuit through timer 288 is open and timer 288 ceases to operate unless switch 290 is in contact with terminal 284. Thus, timer section 254 serves to determine the frequency of operation of timer section 256 by controlling the opening and closing of switch 272 and hence the power current or absence thereof to timer 288. Timer section 256 includes six independently operated cam switches 290, 292, 294, 296, 298 and 300. Switch 292 is connected to terminal 268 of power section 258 and selectively to one of terminals 302 and 304. Switch 294 is connected to terminal 304 and to a selected one of terminals 306 and 308. Switch 296 is connected to terminal 308 and a selective one of terminals 310 and 312. Switch 298 is connected to terminal 268 and a selected one of terminals 314 and 316. Switch 290 is connected to timer 288 and a selective one of terminals 282 and 284, as above described. Terminal 300 is connected to terminal 268 and a selected one of terminals 318 and 320. Terminals 302, 306, 310 and 312 are connected to terminals 322, 324, 326 and 328 of terminal section 264, respectively. Terminals 304, 308 and 312 serve to complete an electrical circuit from terminal 268 to terminal 328 when switches 292, 294 and 296 are connected to terminals 304, 308 and 312, respectively. This circuit causes the actuation of drain valve 82 when sample valve 30, buffer valve 86 and water valve 40 are in the closed position.

Switch 292 serves to complete a circuit to solenoid valve 30 when moved from its normal position in contact with terminal 304 to a second position in contact with terminal 302. This movement serves to break or open the circuit from terminal 268 to solenoid valve 82 when the circuit from terminal 268 to solenoid valve 30 is closed, thus preventing simultaneous opening of solenoid valves 30 and 82. Switch 294 serves to complete a circuit from terminal 268 through terminals 306, 324, 164 and 148 and wires 154 and 161 and buffer solenoid valve 86 to second power terminal 270 and simultaneously to open the circuit from terminal 268 to switch 296 to thereby open the circuit from terminal 268 to either water valve 40 or drain valve 82 when switch 292 is in contact with terminal 306. Switch 294 is disconnected from terminal 268 when switch 292 is in contact with terminal 302, thus preventing simultaneous opening of sample valve 30 and buffer valve 86. Switch 296 serves to close a circuit from terminal 268 through terminals 310, 326, 165 and 149 to water solenoid valve 40 when, and only when, switches 292 and 294 are connected to terminals 304 and 308, respectively. Thus, water solenoid valve 40 is operable only when drain solenoid valve 82, sample solenoid valve 30 and buffer solenoid valve 86 are closed. Switches 292, 294 and 296 thus serve to open only one of solenoid valves 30, 86, 40 and 82. The other three of valves 80, 86, 40 and 42 remain closed. These valves have a built-in priority of the following order: sample valve 296 can be opened at any time and will, when open prevent operation of valves 86, 40 and 82. Only when sample valve 30 is closed, can valve 86, 40 or 82 be opened. Similarly, when sample valve 30 is closed, buffer valve 86 prevents operation of valves 40 and 82 when buffer valve 86 is open. Water valve 40 and drain valve 82 are operable only when sample valve 30 and buffer valve 86 are both closed.

A switch 298 serves to connect terminal 268 with a selective one of terminals 314 and 316. Terminal 316 is an isolated or "dead" terminal while terminal 314 leads to relay section 260. Specifically, terminal 314 leads through wire 330 to coil 332 of relay section 260 and also leads through wire 334 to condenser 336 of auto zero section 262. Thus, when switch 298 is in contact with terminal 314, relay section 260 and auto zero section 262 are actuated to perform an automatic adjustment or standardization of pH meter 126 as described below. When switch 298 is in contact with terminal 316, the relay section 260 and the auto zero section 262 are inactivated.

Switch 290 serves to connect a selective one of terminals 282 and 284 to timer 288. When switch 290 is connected to terminal 282 and from terminal 282 through wire 278 to first timer section 254 as above described, and first timer section 254 is actuated by the closing of timer manual switch 140, timer 288 is actuated and begins the timing sequence. Timer 288 continues to operate until a given point in time when switch 290 is moved from contact with terminal 282 into contact with terminal 284, thus opening the connection from terminal 268 to timer 288 as above described and placing timer 288 in contact through wire 280 with terminal 276. This movement of switch 290 places second timer section 256 in a "ready" position in which second timer section 256 will be actuated upon the movement of switch 272 from contact with terminal 274 into contact with terminal 276 responsive to timer 142. Upon this actuation of switch 272, timer 288 again operates to open and close switches 290, 292, 294, 296, 298 and 300 in proper sequence.

Switch 300 serves to connect first power terminal 268 with a selected one of terminals 318 and 320. Terminal 320 is an isolated or "dead" terminal. Terminal 318 is connected to terminals 338 and 340 of relay section 260 through wire 342. Switch 300 serves to turn pH meter 126 on or off when connected to terminals 318 and 320, respectively. Specifically, switch 300 serves to supply current to terminal 196 of pH meter 126 when switch 300 is in contact with terminal 318 and switch 298 is in contact with terminal 316. When relay section 260 is actuated, switch 300 is over-ridden by the operation of relay section 216 which disconnects terminals 338 and 340 from terminal 196 of pH meter 126, which occurs when switch 298 is in contact with terminal 314.

In order to understand the sequencing of switches 290, 292, 294, 296, 298 and 300, reference should be made to the following table which lists a preferred sequence of operations for second timer section 256.

| SECOND TIMER SECTION SEQUENCE | | |
|---|---|---|
| Time | Switch | Function |
| 0:10–4:15 | 292 | Sample Flow Off |
| 0:15–0:30 | 292, 294, 296 | Drain Cell |
| 0:30–0:45 | 296 | Rinse Cell (Water Flow) |
| 0:45–1:00 | 292, 294, 296 | Drain Cell |
| 1:00–4:00 | 294 | Buffer Electrodes |
| 1:30–3:50 | 298 | pH Meter Standardization |
| 4:00–4:15 | 292, 294, 296 | Drain Cell |
| 4:45–(2–18 hr) | 290 | Timer Off |
| 4:40–Next Cycle | 300 | pH Meter, Recorder On |

Power section 258 comprises first power terminal 268, second power terminal 270, indicator light 342, power switch 138 and fuse 344. Switch 138 is connected to terminal 346 of terminal section 264 which is in turn connected to an external power source such as a 120 volt, 60 hertz alternating current. Switch 138 is also connected to a selected one of terminals 348 and 350 to open or close a circuit leading to first power terminal 268 from terminal 346, respectively. Terminal 350 is connected to first power terminal 268, indicator light 342 and to terminals 194 and 232. Thus, when switch 138 is in contact with terminal 350, current is supplied to first power terminal 268, indicator light 342, pH meter 126 and recorder 128. First power terminal 268 is in turn connected to first timer section 254, second timer section 256, relay section 260 and auto zero section 262 to provide power to operate the control unit 22. Fuse 344 can be any suitable fuse, such as for example a 5 amp standard fuse, in order to protect control unit 22 against overcurrent damage. Indicator light 342 is also connected to second power terminal 270 in order to provide an indication when switch 138 is in contact with terminal 350. Second power terminal 270 is connected to terminals 352, 354 and 356 of terminal section 264 in order to complete the circuit from first power terminal 268 through control unit 22, recorder 128 and pH meter 126 to the external power source above described.

Relay section 260 comprises relay 332, switches 358, 360, 362 and 364 and terminals 366, 338, 368, 340, 370, 372, 374 and 376. Switches 358 and 360 are connected in parallel to terminal 236 of recorder 128. Switches 362 and 364 are connected in parallel to terminal 196 of pH meter 126. Terminals 338 and 340 are connected in parallel to terminal 318 of first timer section 256. Terminals 366 and 368 are connected in parallel to first power terminal 268. Terminals 370 and 374 are connected in parallel to auto zero motor 248 of auto zero section 262. Terminals 372 and 376 are connected in parallel to terminal 238 of recorder 128. Switches 358 and 360 serve to connect a selected pair of terminals 370, 374 and 372, 376 to terminal 236 of recorder 128, in order to either connect the servomotor to the output of the recorder amplifier (not shown) or the output of auto zero motor 248. Switches 362 and 364 serve to connect a selected pair of terminals 338, 340 and 366, 368 to terminal 196 of pH meter 126 in order to connect the standby actuator of pH meter 126 with either first power terminal 268 or terminal 318 of first timer section 256. Coil 332 serves to move switches 358, 360, 362 and 364 from a normal position of contact with terminals 376, 372, 340 and 338, respectively, into contact with terminals 374, 370, 368 and 366, respectively, when coil 332 is actuated by the movement of switch 298 from its normal position of contact with terminal 316 into contact with terminal 314 of first timer section 256. The actuation of coil 332 serves to actuate the auto zero or pH standardization function of control unit 22.

Auto zero section 262 comprises auto zero motor 248, condenser 336 and range control 378. Condenser 336 is preferably a 0.75 microfarad condenser or capacitor suitable for 220 volt alternating current. Auto zero motor 248 is a suitable servomotor means capable of adjusting range control 378 so as to produce a "zero" or midpoint reading of pH meter 126 when switch 298 is moved into contact with terminal 314. Range control 378 comprises a power supply 380 and an electrical range control circuit 382. Power supply 380 is preferably a power converter capable of producing 5 volts direct current from the 120 volts alternating current provided by first and second power terminals 268 and 270. Range control circuit 382 preferably comprises a pair of 560ohm resistors 384 and 386, a pair of 470ohm resistors 386 and 388 and a 100ohm potentiometer 390. Resistors 384 and 386 are connected in series and resistors 386 and 388 are connected in series. Wire 393 is connected between resistors 386 and 388 while wire 394 is connected between resistors 384 and 386 to range control circuit 302. Resistor pairs 384, 386 and 386, 388 are connected in parallel to a common terminal 392 and potentiometer 390. Terminal 392 and potentiometer 390 are in turn connected to terminals 198 and 200 of pH meter 126 in order to adjust the output range of pH meter 126 so as to produce a given pH reading in response to a given signal from electrodes 56, 58 and 62. Wires 393 and 394 are connected to output terminals 396 and 398 of power supply 380 in order to apply voltage to range control circuit 382. Thus, when switch 298 is moved from terminal 316 to terminal 314, auto zero motor 248 adjusts potentiometer 390 in order to apply the proper voltage to terminals 198 and 200 to standardize pH meter 126.

Terminal section 264 comprises terminal groups 400 and 402. Terminal group 400 comprises terminals 163-167, 210, 404, 406, 408, 212, 216, 220, 222, 244, 250 and 252, which are respectively connected to terminals 147-151, terminal 192, the neutral wire of an external power source 410, the hot wire of external source 410, the ground wire of external power source 410, wire 208, terminal 196, terminal 198, terminal 200, terminal 234, terminal 236 and terminal 238. Terminal 408 is also grounded through ground wire 412. Terminal group 402 comprises terminals 322, 324, 326, 328, 352, 354, 356, 346, 414, 416, 418, 420, 422, 424 and 426, which are respectively connected to terminal 302, terminal 306, terminal 310, terminal 312, second power terminal 270, second power terminal 270, second power terminal 270, switch 138, terminal 350, terminals 362 and 364, terminal 392, potentiometer 390, auto zero motor 248, terminals 358 and 360 and terminals 372 and 376. Terminals 322, 324, 326, 328, 352, 354, 356, 346, 414, 416, 418, 420, 422, 424 and 426 are also respectively connected to terminals 163, 164, 165, 166, 167, 210, 404, 406, 212, 216, 220, 222, 244, 250 and 252 of terminal group 400 by suitable wires (not numbered) which can be enclosed within a conduit of any suitable length.

OPERATION

With the above structure in mind, the operation of analyzer 10 will now be described. In normal operation, a sample is withdrawn from the sample source (not shown) through sample means 12 and fed to test chamber 16. The sample fluid overflows and exits through overflow opening 364 and is returned by sample return means 70 to the sample source. pH measuring means 20 is continuously operated during this time to continuously monitor the pH of the sample fluid within test chamber 16 in order to provide a record of said pH.

In order to assure that analyzer 10 provides an accurate record of the pH of the fluid within the sample source, it is advantageous to automatically standardize pH measuring means 20 against a buffer solution of known pH. Buffer supply means 24 selectively provides a buffer solution of known pH to test chamber 16 against which pH measuring means 20 may be periodically standarized by control unit 22. This standardization is accomplished by the operation of control unit 22 which automatically closes solenoid valve 32 to inactivate sample feed means 12 and opens solenoid valve 82 to discharge all sample fluid within test chamber 16. Control unit 22 then closes drain solenoid valve 82 and opens solenoid valve 40 to allow rinse fluid to pass into test chamber 16 and overflow through overflow opening 64 or drain through sample drain means 72, as desired. After a predetermined amount of time, solenoid valve 40 is closed and drain solenoid valve 82 is opened to discharge the rinse fluid from test chamber 16. Then solenoid valve 86 is actuated to introduce buffer solution from bulb 102 into test chamber 16 and pH measuring means 20 is actuated to give a pH indication which can be compared with the known pH of the buffer solution introduced from bulb 102. Auto zero motor 248 is then actuated to automatically adjust this pH reading so as to standardize this pH reading. Following this standardization of pH measuring means 20, solenoid valve 86 is de-energized to prevent further introduction of buffer solution to test chamber 16 and drain solenoid valve 82 is opened to discharge the buffer solution from test chamber 16. Drain solenoid valve 82 is then re-closed and solenoid valve 32 is de-energized to once again allow operation of sample feed means 12 in normal manner to feed sample fluid from the sample source to test chamber 16 for pH moitoring by a now adjusted pH measuring means 20. In this way, accurate continuous monitoring of the pH within the sample source can be accomplished.

With the above overall operation of analyzer 10 in mind, the operation of control unit 22 will be more specifically described. The normal condition of control unit 22 is shown in FIG. 4. The normal condition of control unit 22 is with sample solenoid valve 30 in the open position and buffer solenoid valve 86, rinse solenoid valve 40 and drain solenoid valve 82 all closed so that sample fluid flows continuously to test chamber 16 as above described. This normal condition remains so long as timer manual switch 140 is not actuated or closed because timer auto switch 142 will not begin to operate until timer manual switch 140 is actuated and hence control unit 22 will remain in the normal condition and sample flow will continue through sample feed means 12. Control unit 22 includes two timer sections of different types. First timer section 254 includes timer auto switch 142 which is a single switch type timer and second timer section 256 includes a multiple, cam-operated timer 288 which serves to move switches 290, 292, 294, 296, 298 and 300 from their normal position, as shown in FIG. 4, to a second position which is downward from the normal position as shown in FIG. 4. The timing of each of switches 290, 292, 294, 296, 298 and 300 can be independently set so that the movement of each of said switches is independent of the movement of the other switches of second timer section 256.

When automatic operation of control unit 22 is desired in order to provide analyzer 10 with an automatic buffer standardization, timer manual switch 140 is depressed to actuate timer auto switch 142. Timer auto switch 142 can be set to actuate second timer section 256 with any selected frequency. Second timer 288 proceeds to an on position in response to the actuation of timer manual switch 140 since timer manual switch 140 closes a circuit through switch 290 to timer 288 until such time as timer 288 receives power for a predetermined time and switch 290 is moved from its normal position in contact with switch 282 to a second position in contact with terminal 284. Second timer section 256 is now ready for automatic standardization when switch 272 is moved into contact with terminal 276. At the appropriate time, as preselected, timer auto switch 142 actuates relay 271 to move switch 272 into contact with terminal 276 to begin the automatic standardization. Switch 272 is maintained in contact with terminal 276 by relay 271 during the automatic standardization operation. Once switch 272 is moved into contact with terminal 276, second timer section 256 takes over and controls the automatic standardization by properly sequencing the various components of analyzer 10 in order to achieve this automatic standardization. The sequence is as described above in the table entitled SECOND TIMER SECTION SEQUENCE. When this sequence is complete, switch 290 is moved from its second position in contact with terminal 284 back to its normal position in contact with terminal 282, thus opening the circuit from first power terminal 268 through switches 140, 272 and 290 to timer 288. Timer 288 thus remains in the condition it was in at the time switch 290 so moved and maintains this position until switch 272 is also returned to its normal position in contact with terminal 274. When switch 274 is again in contact with terminal 274, current once again flows between first power terminal 268 and second timer 288 through switches 140, 272 and 290. Timer 288 then continues to operate until switch 290 is once again placed in contact with terminal 284 and thereby second timer section 256 is again placed in a ready position to be actuated by the movement of switch 272 to its second position in contact with terminal 276, as above described. It is therefore seen that the operation of first and second timer sections 254 and 256 will periodically cause analyzer 10 to be automatically standardized, in the manner described above, and that the frequency of such automatic standardization can be set at any desired value.

The solenoid valves 30, 86, 40 and 82 are controlled by second timer section 256 and are connected in a series connection, as described above, in order to prevent simultaneous operation thereof and to assure that only one of solenoid valves 30, 86, 40 and 82 operates at a given time. Simultaneous operation could be provided by connecting each of switches 292, 294 and 296 in parallel with terminal 268 rather than in series, as above described. If such a parallel connection were utilized, an additional switch (not shown) would be necessary to govern the operation of drain solenoid valve 82. However, it is preferred to have the series-type connection rather than a parallel-type connection in order to better assure that the solenoid valves operate sequentially rather than simultaneously.

Auto zero motor 248 serves to perform the actual adjustment of pH measuring means 20 during the automatic standardization. This auto zero motor 248 is actuated when switch 298 is moved from its normal position of contact with terminal 216 to a second position in contact with terminal 314. This switch 298 is moved to its second position by a cam driven by timer 288, said cam being selected so as to move switch 298 at the appropriate time during the standardization process. Relay 332 simultaneously moves switches 358, 360, 362 and 364 from a normal position in contact with terminals 376, 372, 340 and 338 into a second position in contact with terminals 374, 370, 368 and 366, respectively, in response to the movement of switch 298 to its second position. This movement of switches 358, 360, 362 and 364 serves to put pH meter 126 on standby by connecting terminal 268 to terminal 196 through switches 362 and 364. This movement of switches 358, 360, 362 and 364 also serves to connect the amplifier (not shown) of recorder 128 to the input 428 of auto zero motor 248 to set potentiometer 390 at the appropriate position to give a proper voltage signal to terminals 198 and 200 of pH meter 126 in order to modify the signal output at terminals 202 and 204 to produce accurate pH readings. Switches 362 and 364 serve to selectively place pH meter 126 on "standby" when auto zero motor 248 is not on by selectively connecting terminal 196 to terminal 268. This standby operation disconnects the visual indicator of pH meter 126 from its input signal and thereby allows adjustment of the visual indicator by the auto zero motor, as above described.

The buffer solution stored within buffer storage means 88 can be any commercial buffer solution of known pH, such as a buffer solution prepared according to the following composition;

20.32 ml 0.1N HCl + 50 ml 0.1 M $KHC_8H_4O_4$, Diluted to 100 ml and the buffer solution stored in buffer storage means 90 can preferably be a solution prepared according to the following composition:

45.45 ml 0.1N NaOH + 50 ml 0.1 M $KHC_8H_4O_4$, Diluted to 100 ml

Any other similar buffer solution may be utilized. It must be kept in mind that the accuracy of analyzer 10 depends on the accuracy of the buffer solution against which analyzer 10 is standardized.

Control unit 22 could be any automatic valve control device suitable for sequencing sample, buffer, rinse and drain valves in order to control standardization of analyzer 10 automatically. Control unit 22 could, for example, be partly pneumatic or hydraulic, although electrical control is preferred due to its smaller size, greater power economy and generally longer life.

Solenoid valves 32, 40, 82 and 86 could be replaced by any suitable automatic valves which are compatible with the control unit utilized and which provide satisfactory closures and openings of the passages through sample feed means 12, rinse feed means 14, drain means 72 and buffer supply means 24, respectively. If large volumes or high pressures are used, it may be desirable to use pneumatic or hydraulic assisted valves in order to give greater closing and opening forces.

The buffer solution used is preferably a standard buffer solution which is compatible with the particular sample fluid being fed to test chamber 16, although rinse feed means 14 serves to substantially clean test chamber 16 and its associated electrodes 56, 58 and 62. The rinse feed means 14 preferably utilizes water as a rinse medium since water is relatively cheap, of neutral pH and is a good solvent for dissolving residual sample fluid. However, any other rinse medium of a relatively neutral pH and good cleansing ability and which is compatible with the sample fluid being monitored could be utilized.

Analyzer 10 can be used in connection with many chemical reactors to monitor the pH of inlet and outlet streams of various fluids. For example, analyzer 10 could be utilized with an apparatus for production of sodium dithionite ($Na_2S_2O_4$) by reacting sodium amalgam with a sulfur dioxide stream. Specifically, the analyzer of the present invention could be used to monitor the pH of the sulfur dioxide stream in such a process. By way of more specific example, the analyzer of the present invention could be utilized in the apparatus for reacting liquids disclosed in U.S. Pat. No. 3,390,964 issued to A. Wurbs on July 2, 1968, herein incorporated by reference as if set forth at length, to monitor the pH of the sulfur dioxide stream in conduit 9 of said apparatus of the Wurbs patent.

By way of additional example, the analyzer of the present invention could similarly be used in a process for the production of trichloroisocyanuric acid to monitor the discharge stream of trichlorocyanurate and sodium dichlorocyanurate reactor used therein in order to prevent explosive by-product formation of nitrogen trichloride ($NCl_3$). Since the particular process and reactions which occur in each of said sodium dithionite and trichloroisocyanuric acid processes is irrelevant to the operation of analyzer 10, such production processes will not be described in detail. It is only necessary that analyzer 10 be constructed of materials which minimize the likelihood of damage to analyzer 10 from the sample fluids being measured.

While the invention has been described in terms of a preferred embodiment, it will be appreciated by skilled artisans that many modifications can be made within the scope of the invention, and the following claims are intended to cover any and all such modifications within the scope of the invention.

What is claimed is:

1. An apparatus for monitoring the pH of a sample source, comprising:
   a. sample feed means, for selectively withdrawing a fluid sample from said sample source and supplying said withdrawn fluid sample to said apparatus,
   b. test chamber means, in fluid communication with said sample feed means, for receiving said fluid sample and containing said fluid sample during said monitoring,
   c. pH measurement electrode means, for selectively measuring the pH of said contained fluid sample and generating a signal output indicative of said measurement,
   d. sample removal means, for removing said fluid sample from said test chamber means,
   e. automatic buffer standardization means for automatically periodically standardizing said pH measuring means against a buffer solution of known pH, and
   f. automatic zeroing means for automatically adjusting the signal output of said pH measurement electrode means so as to produce accurate pH readings.

2. The apparatus of claim 1, wherein said automatic buffer standardization means further comprises:
   a. rinse feed means, for selectively supplying rinse fluid to said test chamber means,
   b. buffer supply means, for selectively supplying said buffer solution of known pH to said test chamber means,
   c. drain means, for selectively discharging said fluid sample from said test chamber means, and
   d. control unit means, for automatically timing the selective operations of said rinse feed means, buffer supply means and drain means.

3. The apparatus of claim 2, wherein:
   a. said buffer supply means further comprises means for selectively supplying a second buffer solution of a known pH different from the pH of said first buffer solution to said test chamber means and simultaneously preventing supply of said first buffer solution to said test chamber means, and
   b. said pH measuring means comprises a pH meter with at least two output scales, each having a different pH range, and scale selector means for selecting one of said output scales and correlating said output to said pH range of said selected scale.

4. The apparatus of claim 2, wherein:
   a. said pH measuring means has an output scale having a midpoint of a given pH number,
   b. said automatic buffer standardization means further comprises an automatic zeroing means for automatically adjusting said pH measuring means to produce an output reading of said midpoint pH number when measuring said buffer solution of known pH, and
   c. said buffer solution spplied by said buffer supply means to said test chamber has a pH equal to said midpoint pH number.

5. The apparatus of claim 2, wherein said control unit means comprises:
   a. a first timing means for periodically actuating said control unit means at selected intervals of time, and
   b. a second timing means for actuating said rinse feed means, drain means, sample feed means, buffer supply means and pH measuring means in a selected timed sequence so as to automatically standardize said pH measuring means in response to said actuation by said first timing means.

6. The apparatus of claim 2, wherein said sample feed means comprises:
   a. a first conduit in fluid communicaton with said sample source,
   b. a second sample conduit in fluid communication with said test chamber means, and
   c. automatic sample valve means, in fluid communication with said first and second sample conduits, for selectively allowing and preventing passage of fluid from said first sample conduit to said second sample conduit responsive to a signal from said control unit means.

7. The apparatus of claim 6, wherein said rinse feed means comprises:
   a. a first rinse conduit in fluid communication with a source of rinse fluid;
   b. a second rinse conduit in fluid communication with said test chamber means; and
   c. automatic rinse valve means in fluid communication with said first and second rinse conduits, for selectively allowing and preventing passage of rinse fluid from said first rinse conduit to said second rinse conduit responsive to a signal from said control unit means.

8. The apparatus of claim 7 wherein said control unit means includes first switch means for allowing only a selected one of said automatic rinse and sample valves to be open at a given time.

9. The apparatus of claim 7, wherein said buffer supply means further comprises:

a. a first buffer supply conduit in fluid communication with a buffer storage means;

b. a second buffer supply conduit in fluid communication with said test chamber means; and c. automatic buffer supply valve means in fluid communication with said first and second buffer supply conduits for selectively allowing and preventing passage of buffer fluid from said first buffer supply conduit to said second buffer supply conduit responsive to a signal from said control unit means.

10. The apparatus of claim 9, wherein said control unit means includes second switch means for allowing only a selected one of said automatic rinse, sample and buffer supply valves to be open at a given time.

11. The apparatus of claim 9, wherein said drain means further comprises:

a. a first drain conduit in fluid communication with said test chamber means;

b. a second drain conduit in fluid communication with a drain; and c. automatic drain valve means, in fluid communication with said first and second drain conduits, for selectively allowing and preventing passage of drain fluid from said first drain conduit to said second drain conduit responsive to a signal from said control means.

12. The apparatus of claim 11 wherein said control unit means includes third switch means for allowing only a selected one of said automatic rinse, chamber buffer supply and drain valves to be open at a given time.

13. The apparatus of claim 12 wherein said control unit includes first timer means for periodically initiating the automatic standardization of said pH measuring means.

14. The apparatus of claim 13 wherein said control unit further includes a second timer means for sequencing the operation of said rinse feed means, sample feed means, buffer supply means, drain means and pH measuring means so as to automatically standardize said pH measuring means.

15. The apparatus of claim 12 wherein said control unit further includes a second timer means for sequencing the operation of said rinse feed means, sample feed means, buffer supply means, drain means and pH measuring means so as to automatically standardize said pH measuring means.

16. The apparatus of claim 15 wherein said control unit further comprises an auto zero section means for automatically adjusting said pH measuring means to produce a reading of a pH equal to the known pH of said buffer solution when said buffer solution is in said test chamber means and said pH measuring means is measuring the pH of said buffer solution, to thereby automatically standardize said pH measuring means.

17. The apparatus of claim 16 wherein said pH measuring means has an output scale having a midpoint pH number and said pH of said buffer solution of known pH is equal to said midpoint number.

18. The apparatus of claim 16 wherein said control unit further includes a relay section for actuating said auto zero section means responsive to a signal from said second timer.

19. The apparatus of claim 1 further comprising sample return means in fluid communication with said sample source and said test chamber, for returning said withdrawn sample from said test chamber to said sample source.

* * * * *

UNITED STATES PATENT AND TRADEMARK OFFICE
CERTIFICATE OF CORRECTION

PATENT NO. : 4,151,255
DATED : April 24, 1979
INVENTOR(S) : Italo A. Capuano; Edward G. Miller It is certified that error appears in the above-identified patent and that said Letters Patent are hereby corrected as shown below:

On the cover page, column 1, please delete:

" [76]  Inventors:  Italo A. Capuano, Orange; Edward G. Miller, East Haven, both of Conn. "

and insert

--[75]  Inventors:  Italo A. Capuano, Orange; Edward G. Miller, East Haven, both of Conn.

[73]  Assignee :  OLIN CORPORATION, New Haven, Conn.--

Signed and Sealed this

First Day of April 1980

[SEAL]

Attest:

SIDNEY A. DIAMOND

Attesting Officer

Commissioner of Patents and Trademarks